United States Patent
Sharma et al.

(10) Patent No.: US 10,614,294 B1
(45) Date of Patent: Apr. 7, 2020

(54) METHOD AND SYSTEM FOR MEASURING VIEWERSHIP OF PEOPLE FOR DISPLAYED OBJECT

(75) Inventors: Rajeev Sharma, State College, PA (US); Satish Mummareddy, State College, PA (US); Jeff Hershey, Norfolk, VA (US); Hankyu Moon, State College, PA (US)

(73) Assignee: VideoMining Corporation, State College, PA (US)

( * ) Notice: Subject to any disclaimer, the term of this patent is extended or adjusted under 35 U.S.C. 154(b) by 1964 days.

(21) Appl. No.: 11/818,554

(22) Filed: Jun. 14, 2007

Related U.S. Application Data

(60) Provisional application No. 60/814,444, filed on Jun. 16, 2006.

(51) Int. Cl.
*G06K 9/00* (2006.01)
*A61B 5/1171* (2016.01)

(52) U.S. Cl.
CPC ........ *G06K 9/00261* (2013.01); *A61B 5/1176* (2013.01)

(58) Field of Classification Search
CPC .................................................. G06K 9/00261
See application file for complete search history.

(56) References Cited

U.S. PATENT DOCUMENTS

| | | |
|---|---|---|
| 4,972,504 A | 11/1990 | Daniel, Jr. et al. |
| 5,315,093 A | 5/1994 | Stewart |

(Continued)

FOREIGN PATENT DOCUMENTS

| | | | | |
|---|---|---|---|---|
| EP | 0967574 A2 | * | 12/1999 | ......... G06K 9/00228 |
| EP | 1359536 A2 | * | 11/2003 | ......... G06K 9/00275 |

(Continued)

OTHER PUBLICATIONS

I. Haritaoglu and M. Flickner, "Attentive Billboards," 11th International Conference on Image Analysis and Processing, Sep. 26-28, 2001, Palermo, Italy.

*Primary Examiner* — Jacob C. Coppola

(57) ABSTRACT

The present invention is a method and system for measuring viewership of people for a displayed object. The displayed object can be specific in-store marketing elements, such as static signage, POP displays, and other forms of digital media, including retail TV networks and kiosks. In the present invention, the viewership comprises impression level, impression count of the viewers, such as how many people actually viewed said displayed object, average length of impression, distribution of impressions by time of day, and rating of media effectiveness based on audience response. The viewership of people is performed automatically based on the 3-dimensional face pose estimation of the people, using a plurality of means for capturing images and a plurality of computer vision technologies on the captured visual information. The present invention distinguishes viewers from passers-by among the plurality of persons in the vicinity of the displayed object, by counting the number of viewers who actually viewed the displayed object vs. passers-by who may appear in the vicinity of the displayed object but do not actually view the displayed object, using the 3-dimensional face pose estimation and a novel usage of a plurality of computer vision technologies.

11 Claims, 11 Drawing Sheets

(56) References Cited

U.S. PATENT DOCUMENTS

| | | | |
|---|---|---|---|
| 5,331,544 A | 7/1994 | Lu et al. | |
| 6,011,578 A | 1/2000 | Shatto et al. | |
| 6,393,136 B1 * | 5/2002 | Amir et al. | 382/103 |
| 6,526,156 B1 | 2/2003 | Black et al. | |
| 6,539,100 B1 * | 3/2003 | Amir et al. | 382/117 |
| 6,577,329 B1 * | 6/2003 | Flickner et al. | 715/774 |
| 6,661,907 B2 | 12/2003 | Ho et al. | |
| 6,707,933 B1 | 3/2004 | Mariani et al. | |
| 6,741,756 B1 | 5/2004 | Toyama et al. | |
| 6,772,129 B2 | 8/2004 | Alvarez et al. | |
| 6,973,201 B1 | 12/2005 | Colmenarez et al. | |
| 7,035,456 B2 | 4/2006 | Lestideau et al. | |
| 7,043,056 B2 | 5/2006 | Edwards et al. | |
| 7,046,826 B2 | 5/2006 | Toyama et al. | |
| 7,120,880 B1 * | 10/2006 | Dryer et al. | 715/863 |
| 7,643,658 B2 * | 1/2010 | Kilner et al. | 705/14.41 |
| 7,769,632 B2 * | 8/2010 | Giraud et al. | 705/14.4 |
| 2002/0010623 A1 * | 1/2002 | McCollom et al. | 705/14 |
| 2002/0102024 A1 | 8/2002 | Jones et al. | |
| 2002/0116265 A1 | 8/2002 | Hernandez | |
| 2002/0154695 A1 * | 10/2002 | Cornog | H04N 5/145 375/240.16 |
| 2002/0159627 A1 | 10/2002 | Schneiderman et al. | |
| 2003/0098954 A1 * | 5/2003 | Amir et al. | 351/210 |
| 2003/0107649 A1 * | 6/2003 | Flickner et al. | 348/150 |
| 2003/0161500 A1 | 8/2003 | Blake et al. | |
| 2004/0017938 A1 * | 1/2004 | Cooper | G06K 9/00228 382/171 |
| 2004/0240708 A1 | 12/2004 | Hu et al. | |
| 2005/0180626 A1 | 8/2005 | Moon et al. | |
| 2005/0200476 A1 | 9/2005 | Forr et al. | |
| 2005/0203798 A1 | 9/2005 | Jensen et al. | |
| 2005/0265581 A1 | 12/2005 | Porter et al. | |
| 2006/0041480 A1 | 2/2006 | Briggs | |
| 2006/0256133 A1 * | 11/2006 | Rosenberg | G06Q 30/02 345/619 |
| 2007/0076921 A1 * | 4/2007 | Living | G06K 9/00295 382/118 |
| 2011/0208593 A1 * | 8/2011 | Nishida et al. | 705/14.4 |

FOREIGN PATENT DOCUMENTS

| | | | |
|---|---|---|---|
| EP | 1962243 A1 * | 8/2008 | G06K 9/00241 |
| GB | 2409028 A * | 6/2005 | G06K 9/00248 |
| WO | WO 2004051553 A2 * | 6/2004 | G06K 9/00228 |

* cited by examiner

METHOD AND SYSTEM FOR MEASURING VIEWERSHIP OF PEOPLE FOR DISPLAYED OBJECT

CROSS-REFERENCE TO RELATED APPLICATIONS

This application claims the benefit of U.S. Provisional Patent Application No. 60/814,444, filed Jun. 16, 2006.

FEDERALLY SPONSORED RESEARCH

Not Applicable

SEQUENCE LISTING OR PROGRAM

Not Applicable

BACKGROUND OF THE INVENTION

Field of the Invention

The present invention is a method and system for automatically measuring viewership of people for displayed object, such as in-store marketing elements, static signage, POP displays, various digital media, retail TV networks, and kiosks, by counting the number of viewers who actually viewed the displayed object vs. passers-by who may appear in the vicinity of the displayed object but do not actually view the displayed object, and the duration of viewing by the viewers, using a plurality of means for capturing images and a plurality of computer vision technologies, such as face detection, face tracking, and the 3-dimensional face pose estimation of the people, on the captured visual information of the people.

Background of the Invention

There have been earlier attempts to understand the customers' shopping behavior by gathering various market research data or to measure the advertising effectiveness in a targeted environment, such as in a media network or in a retail store.

U.S. Pat. No. 4,972,504 of Daniel, Jr., et al. (hereinafter Daniel, Jr.) and U.S. Pat. No. 5,315,093 of Stewart disclosed market research systems for sales data collection. U.S. Pat. No. 5,331,544 of Lu, et al. (hereinafter Lu) disclosed an automated system for collecting market research data. A computer system remotely located from the plurality of cooperating establishments stores market research data collected from the cooperating establishments. The collected market research data includes monitored retail sales transactions and captured video images of retail customers. The video images of customers are analyzed using a facial recognition system to verify whether the matches to a known gallery of frequent customers are established.

In Lu, the attentiveness measurement was based on the assumption that the shoppers in the acquired images are considered to pay attention to the display, regardless of whether the shoppers actually looked at the display or not. However, this assumption cannot be used as a basis to provide accurate measurement for the attentiveness. Not all the shoppers within a predetermined distance of the display actually look at the display. They could be just passers-by or they could just look at other objects in the vicinity of the display. Therefore it is not appropriate to conclude that the shoppers looked at the display based solely on the fact that they are within the predetermined distance from the display in the acquired images, unless there is an actual measurement that their head orientation is directed exactly toward the display.

Furthermore, Lu presents a comprehensive automated market research solution that utilizes face recognition technology to keep track of shopping behavior of customers. Lu's system is described as typically implemented near checkout counters to capture facial images of customers. The overall idea of using automatic face analysis to extract information about customer behavior is similar between Lu and the presented invention; however, the presented invention aims more on measuring the effectiveness of display material to the viewership of customers, rather than measuring the shopping behavior. The proposed technical solutions exploit the unique settings of the application—customers looking at the display within limited spatial scope—to utilize robust face detection/tracking technology and facial pose estimation.

U.S. Pat. No. 6,011,578 of Shatto, et al. (hereinafter Shatto) disclosed a system for collecting audience response data, using a response unit with dual modes, comprising dial, keypad, and a bi-conditional response mechanism. Clearly, Shatto is foreign to the concept of an automatic and non-cumbersome method for measuring the viewership from the customers without involving any hassle of feeding the information manually by the customers or operator based on computer vision technology.

U.S. Pat. No. 6,772,129 of Alvarez, et al. (hereinafter Alvarez) disclosed a method for determining the effectiveness of advertising media, comprising a step for compiling a total of the number of impressions an advertisement makes. In Alvarez, the term "impression" was defined as the product of the number of viewers multiplied by the number of times they have seen the advertisement. Alvarez disclosed how to use the impression to establish the Net Accumulated Weights ("NAWs") for each media type, and eventually the media effectiveness. Alvarez also briefly introduced the Gross Rating Points (GRPs) by a media research organization as a method for computing impression with a conversion equation. However, Alvarez is clearly foreign to the actual method of calculating the impression, based on the automatic and non-cumbersome actual measurement for the viewership from the customers within the OTS area in the vicinity of a displayed object, utilizing a novel computer vision technology.

U.S. Pat. Appl. Pub. No. 2002/0116265 of Hernandez disclosed an in-store media advertising system, which has a viewer sensor that compiles viewer data, such as the number of viewers and customers in the vicinity of the displayed media content. Hernandez disclosed the usage of a ceiling mounted active infrared matrix sensor as a suitable viewer sensor. In Hernandez, the "customer sensor" monitors the entry and exit of customers and the "viewer sensor" detects how many viewers are in front of the video display. However, Hernandez is also clearly foreign to the distinction between the passers-by and the actual viewers who actually looked at the displayed media content in the vicinity of the displayed media content. The infrared-based viewer sensor does not distinguish between these two in Hernandez. Hernandez disclosed "viewer signals indicating the number of viewers available to view the advertising content" in (Hernandez, paragraph [0009]). Therefore, in Hernandez, the viewer signals only indicate the number of viewers available to view the displayed contents, not the actual measurement of the viewers who actually viewed the displayed contents.

U.S. Pat. Appl. Pub. No. 2005/0200476 of Forr, et al. (hereinafter Forr) disclosed a method and system for monitoring the presence and movements of "participants in market research" in order to carry out traffic flow study and measure the exposure to advertising and promotional activities, using portable monitors carried by the participants. Carrying the monitor around is cumbersome. Forr selected the strength of the transmitted location signal and the sensitivity of the monitor in such a way that the monitor will only detect the signal when it is sufficiently near the identified location. Forr may provide the participants' movement information within a commercial establishment through the location information. However, Forr cannot tell where the true attention of the participants lied in the movement pattern. Since the portable monitors cannot distinguish whether the participant had a particular interest in an object of a location signal or the participant merely happened to pass by the vicinity of the location signal, it is difficult to measure the actual level of impression of the participants to the object of the location signal. Therefore, accurate measurement for the exposure to advertising and its effectiveness cannot be achieved by a simple spatial correlation.

In a U.S. Pat. Appl. Pub. No. 2005/0203798 of Jensen, et al. (hereinafter Jensen), a similar U.S. patent application by two co-inventors out of the Forr, Jensen disclosed a method and system for monitoring exposure of "participants in market research" to predetermined products, utilizing portable monitors with wireless receivers. In Jensen, the participants in market research carry the portable monitors, which detect the product data in the product signal only when in a predetermined proximity to the predetermined signal transmitter. As discussed in Forr, carrying the monitor around is cumbersome. In addition, the monitors cannot tell whether the participants actually looked at the products or just passed by the products within the predetermined proximity, although the monitor provides the location information of the participants. The participants could have stayed within the predetermined proximity not for the predetermined products but for other products in the vicinity of the predetermined products. Therefore, utilizing the portable monitors cannot be a sufficient enough method to accurately measure the exposure of the participants to the intended displayed object or targeted object.

U.S. Pat. Appl. Pub. No. 2006/0041480 of Briggs disclosed a method for determining advertising effectiveness of cross-media campaigns. Briggs' method is to provide media suggestions on each media based on the advertising effectiveness analysis for the cross-media campaigns. Although Briggs disclosed strategic "six basic steps" to assess the advertising effectiveness for multiple media, he is clearly foreign to the concept of actually and automatically measuring the viewership level of an individual or a group of viewers for a displayed object based on the visual information from the viewers.

Haritaoglu, et al. (hereinafter Haritaoglu) in "Attentive Billboards", 11th International Conference on Image Analysis and Processing, Sep. 26-28, 2001, Palermo, Italy, disclosed a real-time computer vision system and algorithms that extracts customer behavior information by detecting and tracking multiple people as they wait and watch advertisements on a billboard or a new product promotion at a stand.

The prior work by Haritaoglu proposed a system similar in terms of target application to the present system. However, the work is very different from the present method in that the prior art makes use of motion difference information and body silhouette information to detect and track people's faces. In the present method, the faces are detected and tracked using methods dedicated to facial image analysis, which are proven technologies both in academia and in industry. The prior work claims that the infrared-based estimation of gaze direction works within the distance of approximately 10 feet from the camera. The short-range requirement for the infrared illumination-based pupil detection technology makes the method impractical in the market environment: and at the same time limits the scope of the application. Since it is not practical to force the customers to stand within a 10-foot distance from the displayed object, the method of using an infrared light source will miss many viewers outside the range but within the opportunity to see (OTS) area in the vicinity of the displayed object. In addition, in order to reliably detect the bright eye on-axis illumination from one of the infrared light sources, which is located close to the camera, the size of the facial images have to be large enough. If the size of the facial images needs to be relatively large, use of multiple cameras become necessary; it is difficult for a single camera to cover the wide OTS area, while acquiring facial images large enough. Furthermore, the additional infrared devices and cameras increase the cost per displayed object. It will be difficult to install the devices so that they are unobtrusive to the customers. Therefore, it is desirable to have a non-obtrusive, cost-efficient, and broad-range means for measuring the viewership of the viewers in the opportunity to see (OTS) area in the vicinity of the displayed object as disclosed in the presented invention In the case of digital display, the current trend is increasing size of the display. Therefore the customers can be expected to watch the display from sufficiently far ranges (more than 15 feet away). The present system utilizes the holistic pattern of the face to detect and measure the attentiveness; it does not have the limitation as long as the customer's faces appear within the view of the camera bigger than about 20×20 pixels in size.

While the above-mentioned prior arts try to understand the customers' shopping behavior by gathering market research data or to measure the advertising effectiveness using cumbersome portable monitors or strategic assessment steps, they are foreign to the concept of actually measuring customer viewership by the impression levels in an opportunity to see (OTS) area, utilizing an efficient 3-dimensional pose estimation technology. Although Lu briefly mentioned the utilization of the images of shoppers to measure the attentiveness, Lu did not differentiate the passers-by from the actual viewers who actually looked at the displayed objects. Automatic measurement of viewership for the displayed objects utilizing a novel 3-dimensional pose estimation by computer vision technology is foreign to any of the prior art.

Computer vision algorithms have been shown to be an effective means for detecting and tracking people. Computer vision technologies also have been shown to be effective in estimating the pose of a human head in the view of the means for capturing images. This allows for the possibility of connecting the visual information from a scene to the measurement of customer viewership and impression level to the displayed objects.

Face Detection

There have been prior attempts for detecting human faces in still images or in videos, such as U.S. Pat. No. 6,661,907 of Ho, et al. (hereinafter Ho) and U.S. Pat. No. 7,035,456 of Lestideau, et al. (hereinafter Lestideau).

U.S. Pat. Appl. Pub. No. 2002/0102024 of Jones, et al. (hereinafter Jones) and U.S. Pat. Appl. Pub. No. 2002/

0159627 of Schneiderman, et al. (hereinafter Schneiderman) disclosed an object detection system.

The proposed method utilizes the unique characteristics of human skin tone to detect candidate facial regions in an image frame and proceeds to further analysis of the region: whether the regions have spatial arrangement of certain shapes of features, as disclosed in Ho and Lestideau. The proposed invention utilizes a machine learning-based detection method, similar to the method disclosed in Jones and Schneiderman. However, the proposed combination of skin tone detection and machine learning-based face detection is designed to help continuity of the person track, because the reliable tracking performance (starting time and ending time of the presence of the face) is crucial in computing the impression. The skin tone detection serves as a means to speed up the face detection, which is a major bottleneck in face processing. The skin tone detection also significantly reduces falsely detected faces from the background; this feature is especially beneficial when the system needs to detect human faces against the complex background present in typical public scenes. The reduction of number of falsely detected faces is crucial in the present application, in that it will in turn speed up the tracking process where possible multiple matches between the current faces and the previously tracked faces need to be resolved. The subsequent machine learning-based face-like pattern detection method is known to be robust, to detect most of the faces in an image.

Face Tracking

There have been prior attempts for tracking human faces in video, using appearance-based cues, such as U.S. Pat. No. 6,526,156 of Black, et al. (hereinafter Black), U.S. Pat. Appl. Pub. No. 2003/0161500 of Blake, et al. (hereinafter Blake), U.S. Pat. No. 6,973,201 of Colmenarez, et al. (hereinafter Colmenarez), and U.S. Pat. Appl. Pub. No. 2005/0265581 of Porter, et al. (hereinafter Porter).

The proposed method utilizes the facial appearance model to keep the identity of people, as in Black and Blake. However, the method does not require offline training or model building; because the application only concerns the presence of frontal faces, it only builds a very simple and fast online model. It does not involve the transformation of the model, as the in-plane rotation is adjusted using the facial geometry correction step. The inventions of Colmenarez and Porter are designed to track multiple faces and keep the person identity at the same time. The proposed invention, however, does not perform explicit tracking, which requires continuity of the tracks; it just makes correspondences between detected faces. Most of these tracking approaches will fail under low frame rates or severe occlusion, however, the proposed method will still be able to track faces under these circumstances.

Facial Pose Estimation

There have been prior attempts for determining the direction to which the human head is facing, such as U.S. Pat. No. 6,707,933 of Mariani, et al. (hereinafter Mariani), U.S. Pat. No. 6,741,756 of Toyama, et al. (hereinafter Toyama), U.S. Pat. No. 7,043,056 of Edwards, et al. (hereinafter Edwards), U.S. Pat. No. 7,046,826 of Toyama, et al. (hereinafter Toyama 7046826), U.S. Pat. Appl. Pub. No. 2004/0240708 of Hu, et al. (hereinafter Hu), and U.S. Pat. Appl. Pub. No. 2005/0180626 of Moon, et al. (hereinafter Moon).

The prior invention of Mariani solves the problem of facial pose estimation by comparing the relative positions of the facial features, most notably the nose. The estimates put the yaw and pitch of the face in discrete pose bins; ('left', 'frontal', 'right') and ('up', 'normal', 'down'), where the resolution is not enough to determine whether the person is actually facing the display.

The invention of Toyama builds an explicit parametric (Gaussian) statistical model of the facial feature appearance using training data. The success of the method depends on rough alignment of facial features to the models; misalignment can potentially cause a large degree of error. The present method compares the input patterns against a number of model patterns to compute the likelihood of the given pattern whether it is to be from the model patterns. Each likelihood computation is robust due to the use of learning machines.

There are prior inventions on estimating eye gaze, such as Edwards, to measure the person's degree of attention; measuring eye gaze usually requires close range, high-resolution images. The proposed method is designed to perform well using far-range, low-resolution images, because it learns the relationship between the out-of plane rotation of the face and the changes in the holistic pattern of facial features.

The invention by Toyama (7046826) estimates the face orientation by comparing the head position and facial position. The method is also susceptible to errors due to the errors in head or face localization, and is only able to compute relative estimates, whereas the present method is able to produce absolute (yaw, pitch) angle, because the system is designed and trained to output absolute (yaw, pitch) angles.

The head pose estimation method by Hu uses component detectors to first locate facial features, and compute the facial pose, which poses a risk of large error when the component detectors fail. The proposed method learns holistic pattern to estimate the pose; it does not involve such risk.

The method by Moon is similar to the proposed method in terms of learning the global patterns on a large number of facial images using a machine learning technique; however, learning the whole space of patterns using a single machine is not regarded as efficient due to the wide range of pose variation. The present method overcomes this weakness by using a plurality of learning machines, each of which is specialized to a given pose range. The approach has not been adopted for facial pose estimation in the field, to the best knowledge of the inventors.

The invention automatically and unobtrusively analyzes the customers' pose information without involving any hassle of feeding the information manually by the customers or operator. Based on the pose information by the novel approach, the invention measures the viewership and the impression level of customers to the displayed object, and the length of time in which the customers actually looked at the displayed object. It is an objective of the present invention to provide an efficient and robust solution that solves the aforementioned problems in the prior art.

SUMMARY

The present invention is a method and system for automatically measuring viewership of people for a displayed object by counting the number of viewers and the duration of viewing by the viewers. In the present invention, the displayed object comprises in-store marketing elements, static signage, POP displays, various digital media, retail TV networks, and kiosks. In the present invention, the viewership also comprises impression level, impression count of the viewers, such as how many people actually viewed said displayed object, average length of impression, distribution of impressions by time of day, and rating of media effectiveness based on audience response.

The present invention provides viewership measurement programs for various displayed objects, including digital and static signage and point of purchase displays in public spaces. These measurement services provide an understanding of viewership size, as well as the size of the potential viewership. In addition to measuring actual viewers, those who had an opportunity to view, and the relationship between these two groups, present invention measures the duration of viewing among actual viewers.

Potential Viewership

The present invention measures the potential viewership for a displayed object, or those with an opportunity to see, by tracking the behavior of persons around a given displayed object. The present invention employs systems utilizing a means for capturing images, which are generally placed to view persons from above, to collect information about the viewers' proximity to a displayed object. Using this method, the present invention provides data on those who were in the vicinity of, and had an opportunity to view, a displayed object. In the past, opportunity to see has been used as a measure of displayed object effectiveness and reach. While the present invention can measure actual viewership, opportunity to see is still a useful measure—particularly when evaluating the ratio of potential audience to actual viewership.

Actual Viewership

Measurement of the actual viewership for a displayed object (the total number of impressions) is carried out using a forward facing means for capturing images that detects when persons are viewing the screen. An impression is counted when a person has looked in the direction of the screen for a predetermined, minimum amount of time, Page 22 as defined in conjunction with client. The sum total of impressions for a displayed object constitutes the actual viewership for that displayed object. Measurement of actual viewership provides the basis for establishing the value of a displayed object using traditional media valuation terms, such as CPM or cost per thousand impressions. Prior, opportunity to see, or traffic around a displayed object, was commonly used to extrapolate the true viewership of a displayed object.

Impression Length

In addition to counting impressions, the present invention provides information about the duration of these impressions. These durations, or impression lengths, are useful in gauging viewer engagement with a particular displayed object or content being delivered at the time of the impression. Network programmers and advertisers can fine-tune their content to match the typical impression length of a given displayed object or series of displayed objects.

The present invention utilizes a combination of skin tone detection and pattern-based face detection to correctly detect faces in complex backgrounds, so that the subsequent tracking method can accurately mark the entrance and exit times. The continuity of tracks is achieved by the combination of the reliable face detection from the previous step, and the appearance/geometry-based face matching. The stage of 3-dimensional pose estimation utilizing the changes in holistic pattern of faces helps to determine the degree of attention (even when the person looks at the displayed object from a distance), so that the system can achieve a more meaningful measurement of the impression. These methods are streamlined in a unique way so that the counting of impressions and the measurement of the duration of an impression can be reliably carried out.

It is an objective of the present invention to measure the viewers who actually viewed the displayed object by separating them from the passers-by who may appear in the vicinity of the displayed object but do not actually view the displayed object.

In order to separate the actual viewers from the passers-by, the present invention uses a plurality of means for capturing images and a plurality of computer vision technologies, such as face detection, face tracking, and the 3-dimensional face pose estimation of the people, on the captured visual information of the people.

It is another objective of the present invention to aim at measuring the effectiveness of a displayed object to the viewership of customers. The proposed technical solutions exploit the unique settings of the application—customers looking at the displayed object within a limited spatial scope—to utilize robust face detection/tracking technology and facial pose estimation.

It is another objective of the present invention to measure the viewership from the customers, without involving any hassle of feeding the information manually by the customers or operator or any hassle of carrying around a monitoring device, through the presented, non-cumbersome method based on computer vision technology.

It is another objective of the present invention to provide the viewership information for the calculation of market research statistical data, media consumption measurement, meaningful criteria for a rating system, and advertisement effectiveness, such as cost per thousand (CPM). It is a further objective of the present invention to analyze the stopping power of the displayed object based on the viewership information of viewers.

It is another objective of the present invention to allow flexibility in installation location of the measuring device. Unlike the infrared-based method, the means for capturing images in the present invention can be placed flexibly near the displayed object, because the 3-dimensional pose estimation method in the present invention can automatically correct the viewing angle offset between the means for capturing images and the displayed object.

DRAWINGS—FIGURES

DETAILED DESCRIPTION OF THE INVENTION

Figure 1:
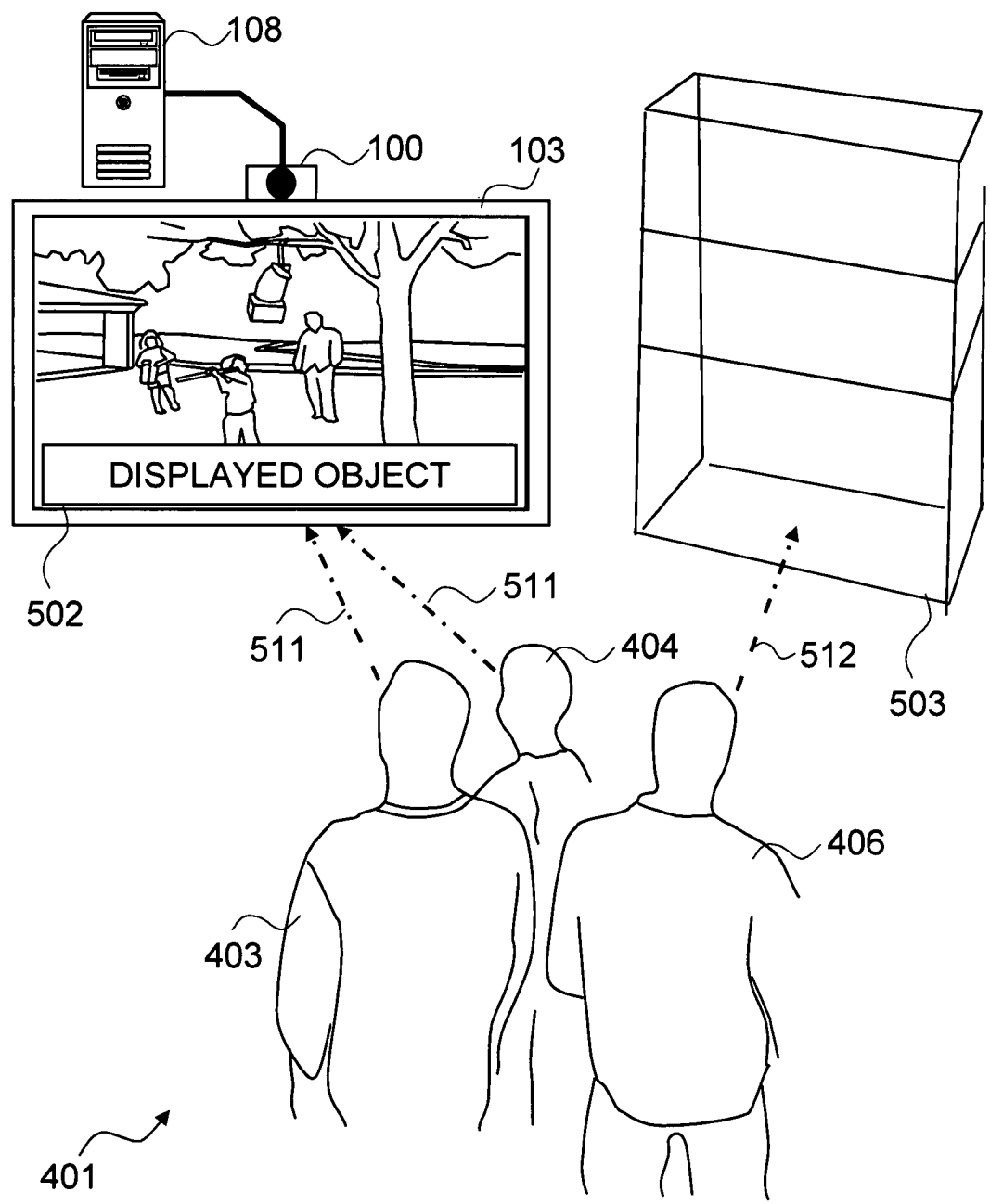
FIG. 1 shows an overview of an exemplary embodiment of the present invention.

FIG. 1 shows an overview of an exemplary embodiment of the present invention. The present invention is a method and system for automatically measuring viewership of people for a displayed object 502 by counting the number of viewers and the duration of viewing by the viewers. In the exemplary embodiment shown in FIG. 1, the displayed object 502 can comprise in-store marketing elements, static signage, POP displays, various digital media, retail TV networks, and kiosks. The displayed object 502 can also comprise the media content shown on the means for playing output 103. In the present invention, the viewership also comprises impression level, impression count of the viewers, such as how many people actually viewed said displayed object 502, average length of impression, distribution of impressions by time of day, and rating of media effectiveness based on audience response. The viewership information can be used to analyze the stopping power of the displayed object. For example, in an exemplary embodiment, any particular increase in the impression count with an additional displayed object indicates the stopping power of the additional displayed object. In another exemplary embodiment, the increased average length of impression can also indicate the stopping power of a particular displayed object.

When a plurality of persons 401 appears in the opportunity to see (OTS) area, the means for capturing images 100 captures the images from the plurality of persons 401. The captured images are processed by the control and processing system 108, such as a computer system, which applies a plurality of computer vision technologies, such as face detection, face tracking, and the 3-dimensional face pose estimation of the people, to the captured visual information of the plurality of persons 401.

In the exemplary embodiment, the present invention measures the number of viewers who actually viewed the displayed object 502 by separating them from the passers-by who may appear in the vicinity of the displayed object 502 within the opportunity to see (OTS) area but do not actually view the displayed object 502. For example, in the exemplary embodiment shown in FIG. 1, the "person A" 403 and the "person B" 404 are viewers, while the "person D" 406 is just a passer-by. It is because Page 27 viewing from the "person A" 403 and the "person B" 404 are measured as the "attentive viewership for the displayed object" 511, while the viewing from the "person D" 406 is a general looking 512 to a nearby object 503.

In the exemplary embodiment, the present invention also measures the effectiveness of the displayed object 502 to the viewership of customers. The proposed technical solutions exploit the unique settings of the application—customers looking at the displayed object 502 within limited spatial scope—to utilize robust face detection/tracking technology and facial pose estimation.

In the exemplary embodiment as shown in FIG. 1, the present invention measures the viewership from the plurality of persons 401 without involving any hassle of feeding the information manually by the plurality of persons 401 or operator, or any hassle of carrying around a monitoring device, through the presented non-cumbersome method based on computer vision technology. The viewership information can be used for the calculation of market research statistical data, media consumption measurement, meaningful criteria for a rating system, and advertisement effectiveness, such as the cost per thousand (CPM), in the exemplary embodiment of the present invention.

Figure 2:
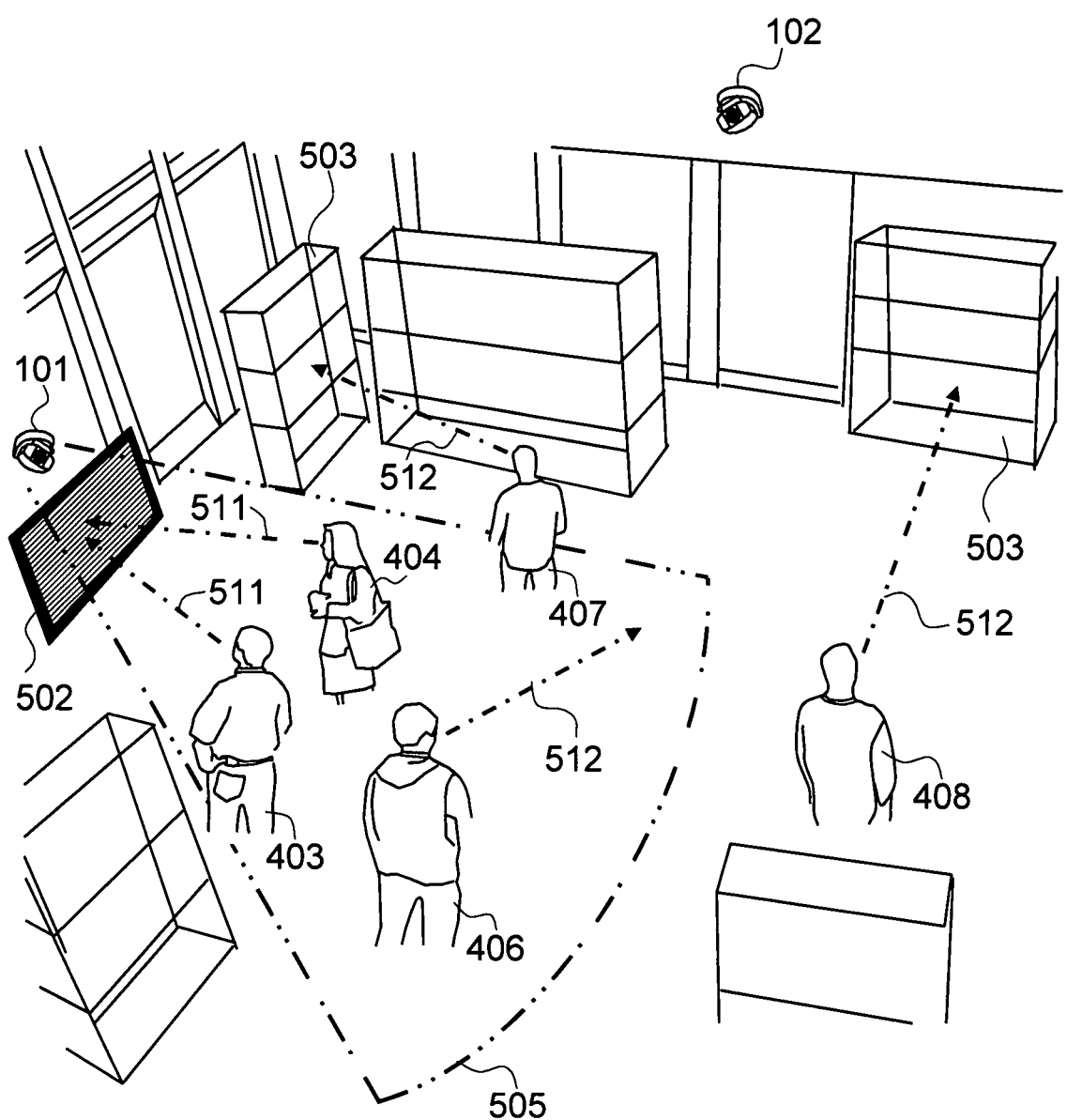
FIG. 2 shows an overview of another exemplary embodiment of the present invention.

FIG. 2 shows an overview of another exemplary embodiment of the present invention. In the exemplary embodiment as shown in FIG. 2, the present invention comprises a first means for capturing images 101 and a second means for capturing images 102. The second means for capturing images 102 detects and tracks a plurality of persons 401 in the vicinity of the displayed object 502 and outside the opportunity to see area 505. In the exemplary embodiment shown in FIG. 2, the present invention distinguishes the viewers, the "person A" 403 and the "person B" 404, from the passers-by, the "person D" 406 and the "person E" 407, and from the outsider, the "person F" 408. It is because viewing from the "person A" 403 and the "person B" 404 are measured as the "attentive viewership for the displayed object" 511, while the viewing from the passers-by, the "person D" 406 and the "person E" 407, and from the outsider, the "person F" 408 is a general looking 512 to a nearby object 503. Although the passers-by, the "person D" 406 and the "person E" 407, are within the opportunity to see (OTS) area unlike the outsider, the "person F" 408, they are still non-viewers.

Potential Viewership

The present invention measures the potential viewership for a displayed object 502, or those with an opportunity to see, by tracking the behavior of persons around a given displayed object 502. The present invention employs systems utilizing a means for capturing images 100, such as the second means for capturing images 102, which are generally placed to view persons from above, to collect information about the viewers' proximity to a displayed object 502. In the exemplary embodiment as shown in FIG. 2, the second means for capturing images 102 can be used for this purpose. Using this method, the present invention provides data on those who were in the vicinity of, and had an opportunity to view, the displayed object 502. In the past, opportunity to see has been used as a measure of displayed object effectiveness and reach. While the present invention can measure actual viewership, opportunity to see is still a useful measure—particularly when evaluating the ratio of potential audience to actual viewership.

Actual Viewership

Measurement of the actual viewership for the displayed object 502 (the total number of impressions) is carried out using a forward facing means for capturing images that detects when persons are viewing the screen. In the exemplary embodiment as shown in FIG. 2, the first means for capturing images 101 can be used for this purpose. An impression is counted when a person has looked in the direction of the screen for a predetermined amount of time, as defined in conjunction with client. The sum total of impressions for a displayed object 502 constitutes the actual viewership for that displayed object 502. Measurement of actual viewership provides the basis for establishing the value of a displayed object 502 using traditional media valuation terms, such as CPM or cost per thousand impressions. Prior, opportunity to see, or traffic around a displayed object 502, was commonly used to extrapolate the true viewership of a displayed object 502.

Impression Length

In addition to counting impressions, the present invention provides information about the duration of these impressions. These durations, or impression lengths, are useful in gauging viewer engagement with a particular displayed object 502 or content being delivered at the time of the impression. Network programmers and advertisers can fine-tune their content to match the typical impression length of a given displayed object 502 or series of displayed objects.

In the exemplary embodiment as shown in FIG. 2, the present invention allows the flexibility in installation location of the measuring device, such as the first means for capturing images 101. Unlike the infrared-based method, the first means for capturing images 101 in the present invention can be placed flexibly near the displayed object 502, because the 3-dimensional pose estimation method in the present invention can automatically correct the viewing angle offset between the means for capturing images and the displayed object 502.

Figure 3:
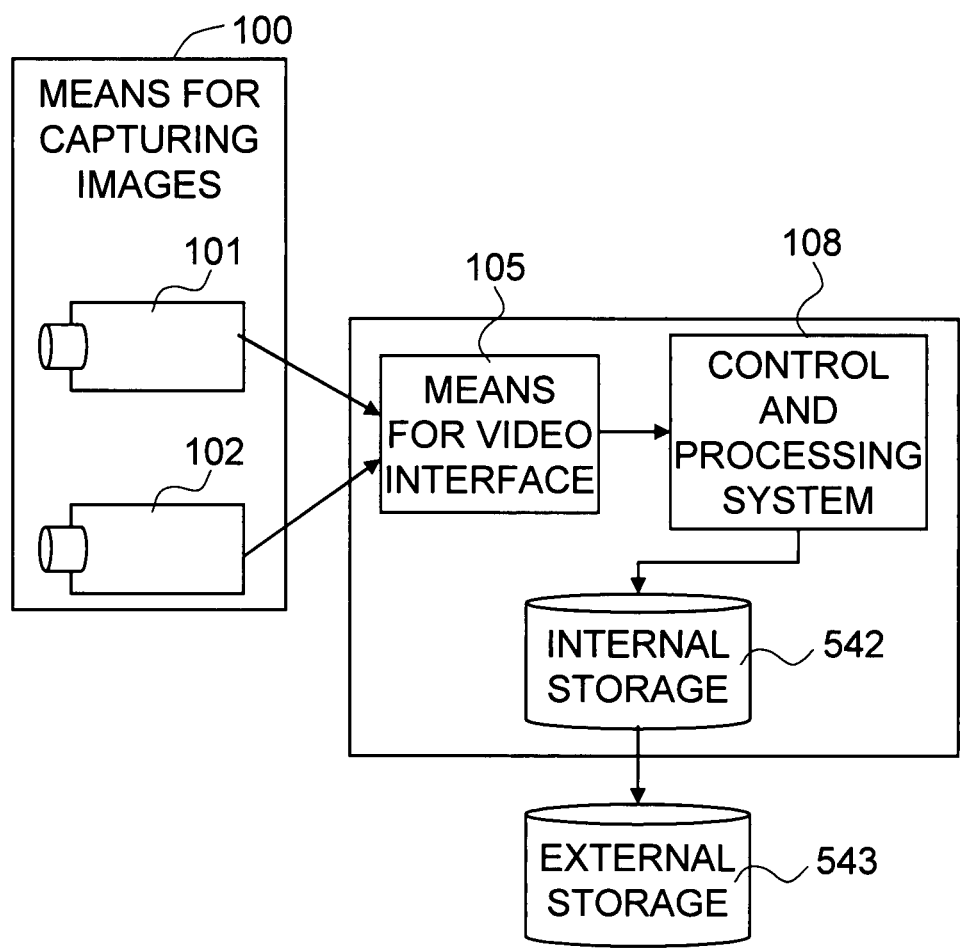
FIG. 3 shows exemplary hardware components in an exemplary embodiment of the present invention.

FIG. 3 shows exemplary hardware components in an exemplary embodiment of the present invention. In an exemplary embodiment of the present invention, the means for capturing images 100 is connected to the means for video interface 105. In the exemplary embodiment shown in FIG. 3, a plurality of means for capturing images 100, the first means for capturing images 101 and the second means for capturing images 102 are connected to the means for video interface 105. The control and processing system 108 takes digitized video data from the means for video interface 105. The control and processing system 108 can have internal means for storing data 542 or external means for storing data 543.

The first means for capturing images 101 can be installed anywhere near the displayed object 502, and they are connected to the means for video interface 105 through cables. The means for capturing images 100 can comprise an analog camera, USB camera, or Firewire camera. The means for video interface 105, which can comprise a video frame grabber, USB interface, or Firewire interface, are typically included in the same enclosure as the control and processing system 108. The control and processing system 108 can be a general-purpose personal computer, such as a Pentium 4 PC, or a dedicated hardware that can carry out the required computation. The control and processing system 108, as well as the means for video interface 105, can be placed locally or remotely, as long as the connection to the means for capturing images 100 can be established. The internal means for storing data 542, such as internal hard disks, is placed within the same enclosure as the control and processing system 108. The external means for storing data 543, such as network storage driver or internal hard disks contained in a remote computer, can be placed locally or remotely, as long as a means for transferring data is available.

In an exemplary embodiment, a general-purpose USB webcam can serve as the means for capturing images 100. A Pentium 4 2.8 GHz PC having 1 GB memory can serve as a control and processing system 108, where a generic USB interface included in the PC's motherboard can serve as a means for video interface 105. A generic IDE hard disk drive can serve as the internal means for storing data 542 or the external means for storing data 543.

Figure 4:
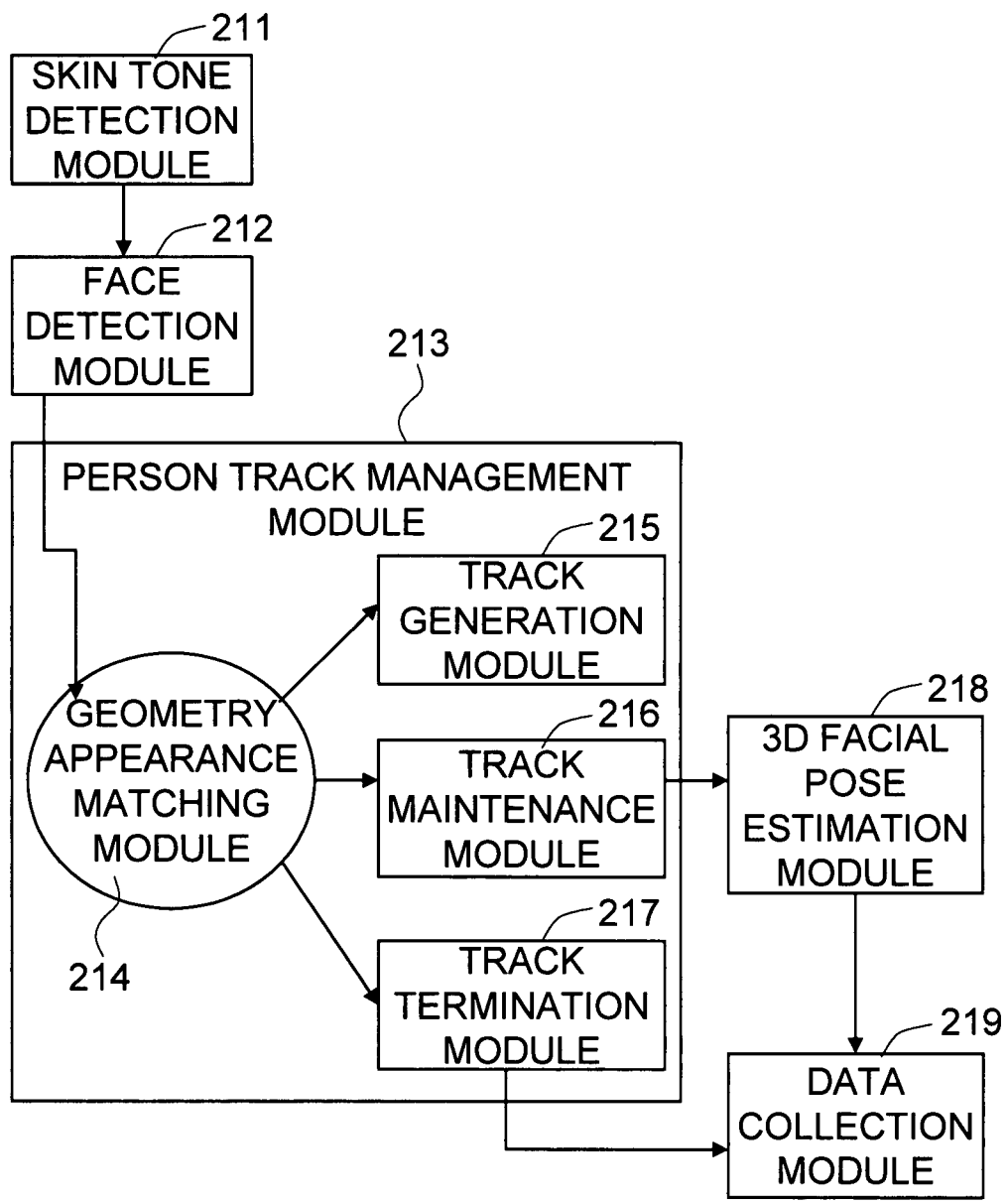
FIG. 4 shows exemplary software components in an exemplary embodiment of the present invention.

FIG. 4 shows exemplary software components in an exemplary embodiment of the present invention. The software components comprise the skin tone detection module 211, face detection module 212, person track management module 213, 3-dimensional facial pose estimation module 218, and data collection module 219. The person track management module 213 further comprises geometry/appearance matching module 214, track generation module 215, track maintenance module 216, and track termination module 217.

The skin tone detection module 211 determines the region in the image frame that is similar to the facial skin tone. The face detection module 212 then runs the face detection window over the regions determined by the skin detection module 211. The detected faces are first processed by the geometry/appearance matching module 214 to determine if the faces belong to the existing tracks or if some of the faces are new, so that a new track can be generated. If the face is new, then the new track generation module 215 is activated to generate a new track and put it in the queue of tracks. If the face belongs to an existing track, then the track maintenance module 216 takes the track data, and activates the 3-dimensional facial pose estimation module 218. If the geometry/appearance matching module 214 cannot find subsequent faces that belong to some track, then the track termination module 217 is activated to store the track data and remove the track from the memory queue. The data collection module 219 then records the track data along with the estimated facial pose data.

The processing software component may be written in a high-level computer programming language, such as C++, and a compiler, such as Microsoft Visual C++, may be used for the compilation in the exemplary embodiment.

Figure 5:
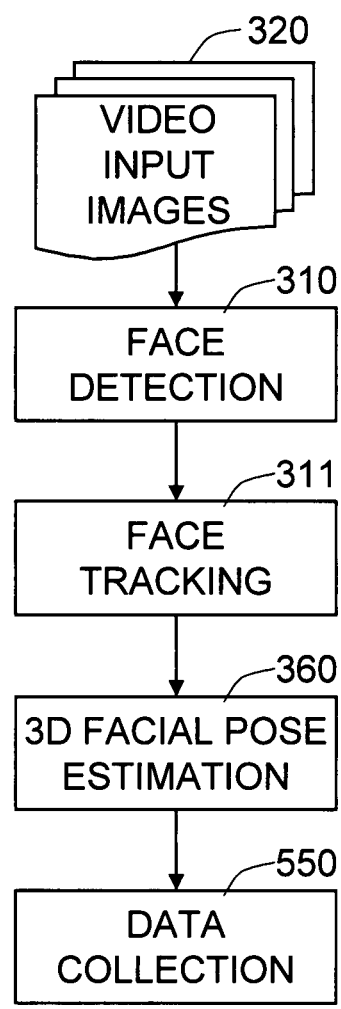
FIG. 5 shows an overview of exemplary viewership measurement processes in an exemplary embodiment of the present invention.

FIG. 5 shows an overview of exemplary viewership measurement processes in an exemplary embodiment of the present invention. In the exemplary embodiment, the system aims to automatically assess the viewership for the displayed object 502, by processing the video input images 320 from a means for capturing images 100, such as the first means for capturing images 101, located nearby the displayed object 502. The system takes live video as an input, detects 310 people's faces in the video, individually tracks 311 them by keeping identities, estimates 360 the 3-dimensional facial pose, time-stamp the appearance and disappearance, and collects 550 the data; it effectively collects the occurrence of viewership and the impression time. For this embodiment, a general-purpose color video camera can be used as the means for capturing images 100 to deliver video frames to the computer via USB or IEEE1394 connection. In the exemplary embodiment, the camera can be placed flexibly near the displayed object 502, because the 3-dimensional pose estimation method can automatically correct the viewing angle offset between the camera and the displayed object 502.

Figure 6:
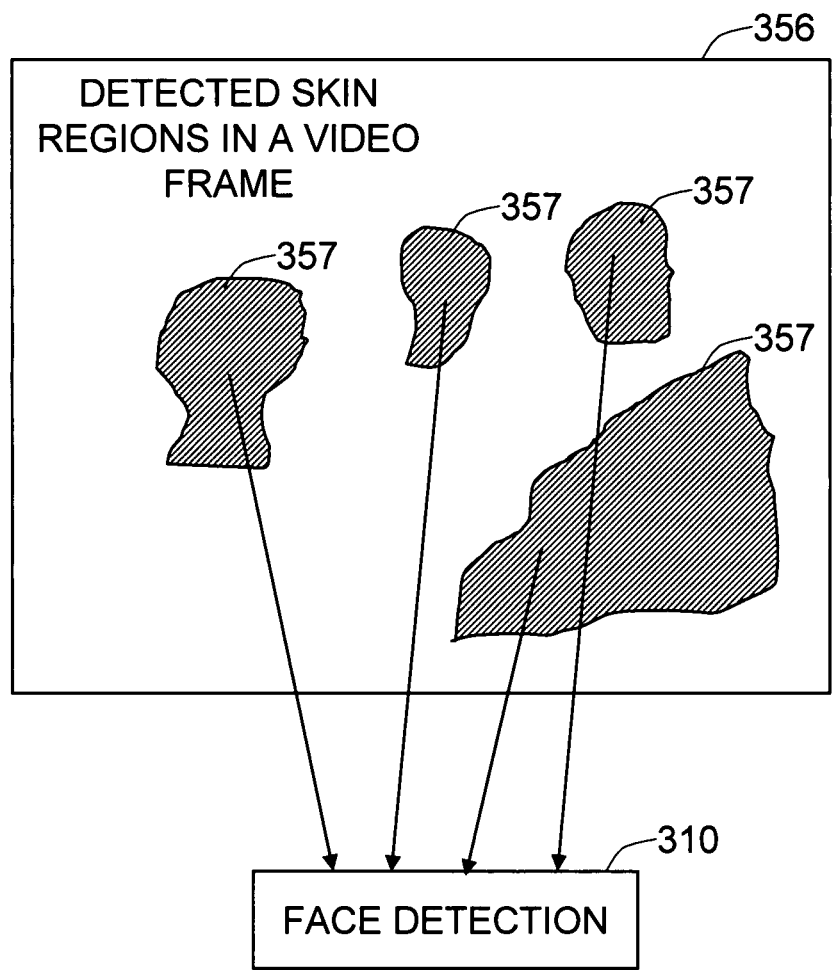
FIG. 6 shows an exemplary face detection process in an exemplary embodiment.

FIG. 6 shows an exemplary face detection 310 process in an exemplary embodiment. In the exemplary embodiment, the present invention first processes the skin tone segmentation 356. At the skin tone segmentation 356 step, the module first segments out the area, detected skin region 357, in the video frame where the human faces are likely to be present, using color information. The scheme utilizes a color space transformation, so that the skin tone forms a compact region in the transformed space. The skin tone detection serves as a means to speed up the face detection 310, which is a major bottleneck in face processing. The skin tone detection also significantly reduces falsely detected faces from the background; this feature is especially beneficial when the system needs to detect human faces against the complex background present in typical public scenes. The output from this step is a collection of masked regions in the video frame.

Next, a face detection 310 process follows. A machine learning-based approach is employed to detect faces within the skin tone region determined by the previous step. This step operates on an image converted to gray scale to detect faces. The step provides the system with the locations and sizes of detected faces in the given video frame.

Figure 7:
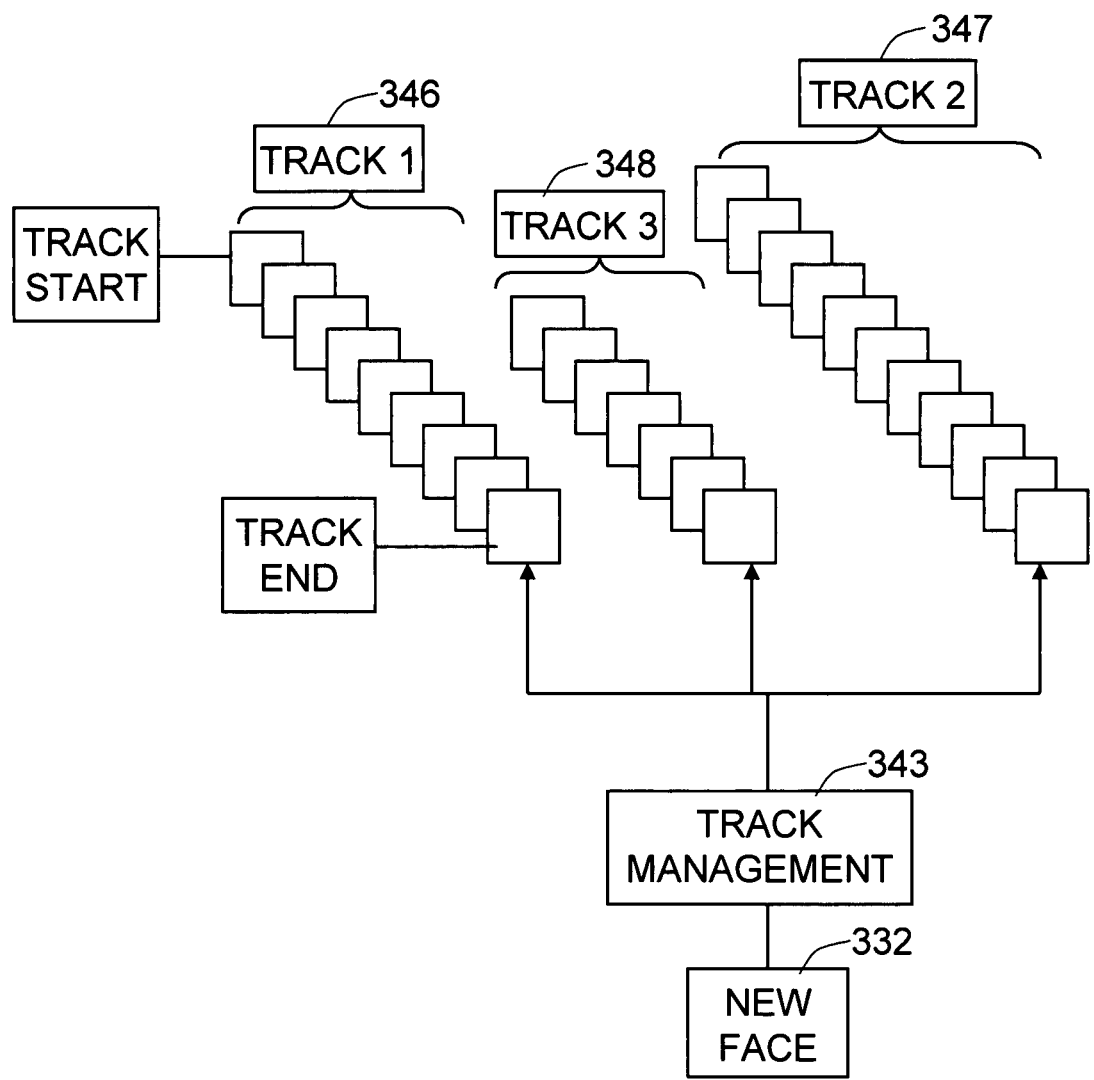
FIG. 7 shows an exemplary face tracking process in an exemplary embodiment, based on facial geometry estimation and appearance model building.
Figure 8:
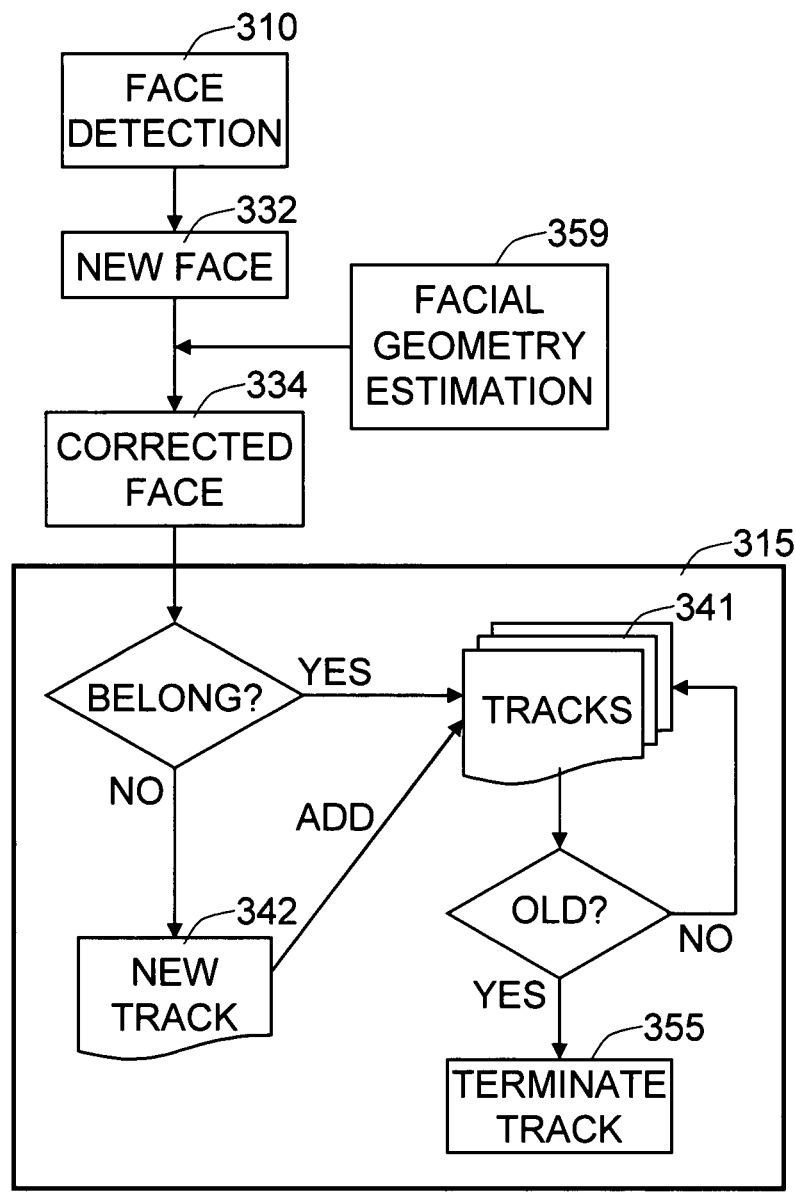
FIG. 8 shows an exemplary track management and verification of the face tracking process in an exemplary embodiment.

FIG. 7 and FIG. 8 show an exemplary face tracking process in the exemplary embodiment, based on facial geometry estimation and appearance model building. In the exemplary embodiment shown in FIG. 8, once a face is detected 310, it goes through the automatic facial geometry correction step 359. This step is necessary because the faces detected from the face detection 310 algorithm have some range of positional and size errors. The detector also accepts modestly tilted faces, and largely ignores such variation. These geometric parameters (position, size, orientation) are estimated using a novel facial geometry estimation 359 scheme. The subsequent appearance-based tracking step has a significant benefit when multiple people are watching the displayed object 502 and when it is hard to resolve a person from others.

The estimated facial geometry is used to generate the corrected face 334 from the detected face image 332 so that the facial features are placed on standard locations in the 30×30 cropped face image chip. This step greatly helps to build a reliable facial appearance model across the track of a person, so that the given input face has a correct match to one of the accumulated models of the people present in the scene. Each time a face is added to a person track, the system builds the appearance model of the person by computing the pixel average image of the entire face image chips in the track.

FIG. 7 and FIG. 8 also show an exemplary track management 343 and face track verification 315 of the face tracking process in an exemplary embodiment. In the exemplary embodiment of the present invention, the tracking step serves as a means to keep the identity of a person in the scene. The system then has a reliable measurement of time and duration of the person watching the displayed object 502. The tracking utilizes two measurements: the geometric and appearance match between the track history and the newly detected face. The track management 343 serves as a means to generate 342 a track when a new face 332 appears in the scene, assign detected faces to tracks to keep identities of people, and to terminate 355 a track when the person is out of the scene.

When new faces are detected in the current video frame, the track management 343 constructs a table of faces and tracks. Then it computes the geometric match and appearance match scores of each (face, track) pair that measure the likelihood of the given face belonging to the given track.

The geometric match score is based on difference in the position, size, and the time between the corrected face 334 and the last face in the track.

The appearance match score measures the difference between the average face appearance stored in the track, and the corrected face 334. If the total score is below a predetermined threshold, the pair is excluded from the table. The pair having the highest score gets the assignment: from the face to the track. The procedure is repeated until all the faces are assigned matching tracks.

However, if there is a new person in the scene, the face is not supposed to have a match to existing tracks. In that case the threshold should have excluded the face, and the face should remain in the queue. The face then generates a new track, and the track is added to the list of tracks. For every frame, if a certain track did not have a new face 332 for more than a pre-specified time period, the track management 343 terminates the track.

Figure 9:
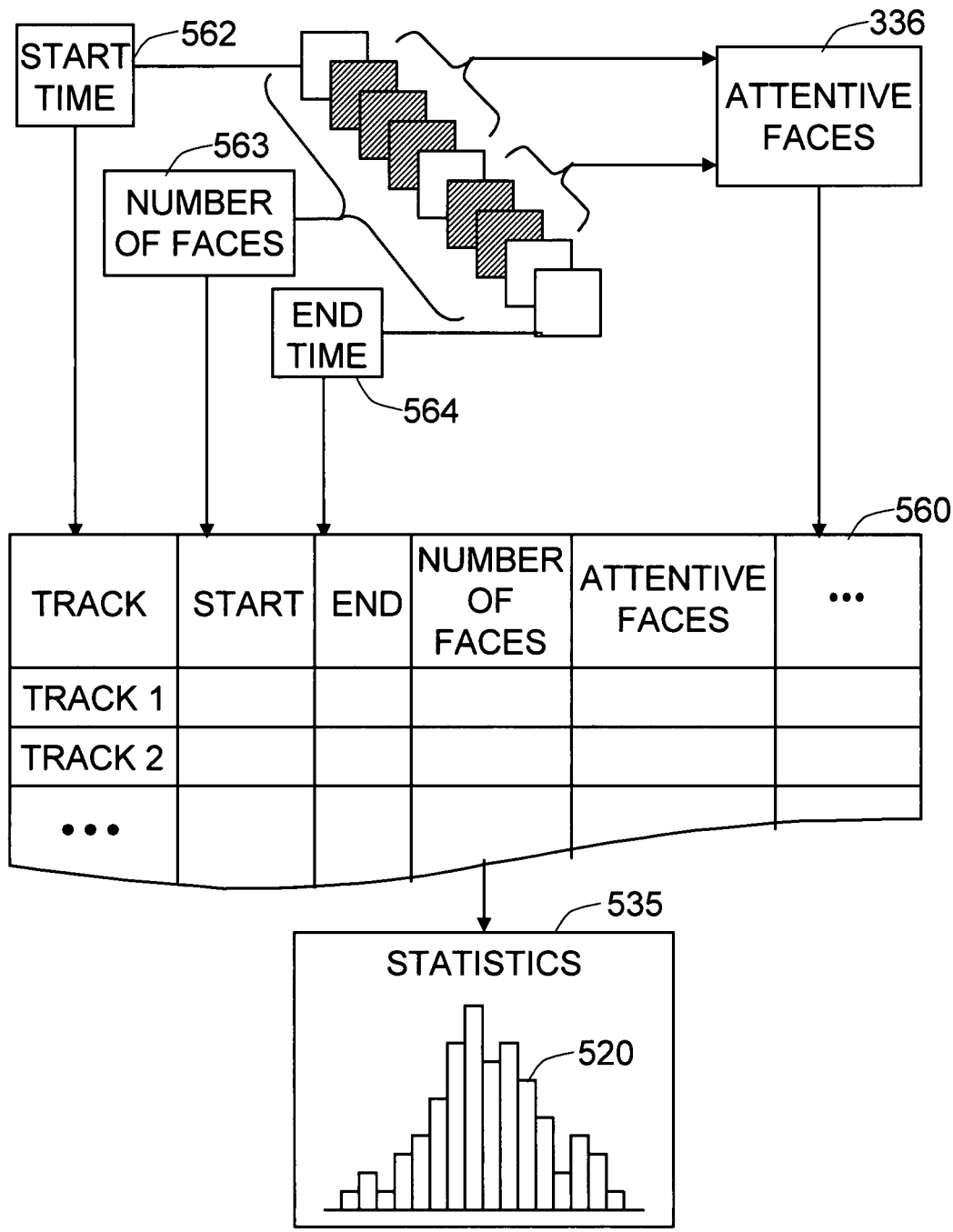
FIG. 9 shows an exemplary data collection in an exemplary embodiment of the present invention.

FIG. 9 shows an exemplary data collection in an exemplary embodiment of the present invention.

Recording of Appearance and Disappearance Time

In the exemplary embodiment, a completed track can provide all the necessary information to assess the viewership of the displayed advertisement. The start time 562 and the end time 564 of the track are recorded, and the difference between the two time stamps represents the total impression time.

Assessment of Attentive Viewership

The system has an added feature to accurately measure the degree of attention during the customer viewing period by computing the proportion of the time when the viewer paid attention to the displayed object 502 out of the total duration of the person's face. The face detection 310 step detects faces having a near-frontal pose, however, there are no guarantees that a person is actually looking at the screen at the moment. The system utilizes a novel 3-dimensional facial pose estimator to have a very good assessment of the viewership. The system can determine whether the face is truly frontal, based on the estimated facial orientation. Once the track is complete, the ratio of the number of frontal faces out of the number of the detected faces is computed.

Collection of Statistics

The system can store the data as a table 560, where each track has fields of values: time stamps, the start time 562 and the end time 564 of the track for the appearance and disappearance of the face, the number of faces 563, and the number of attentive faces 336. The data is used to collect statistics 535, such as the histogram 520 of impression, the number of viewers as a function of time, etc.

Figure 10:
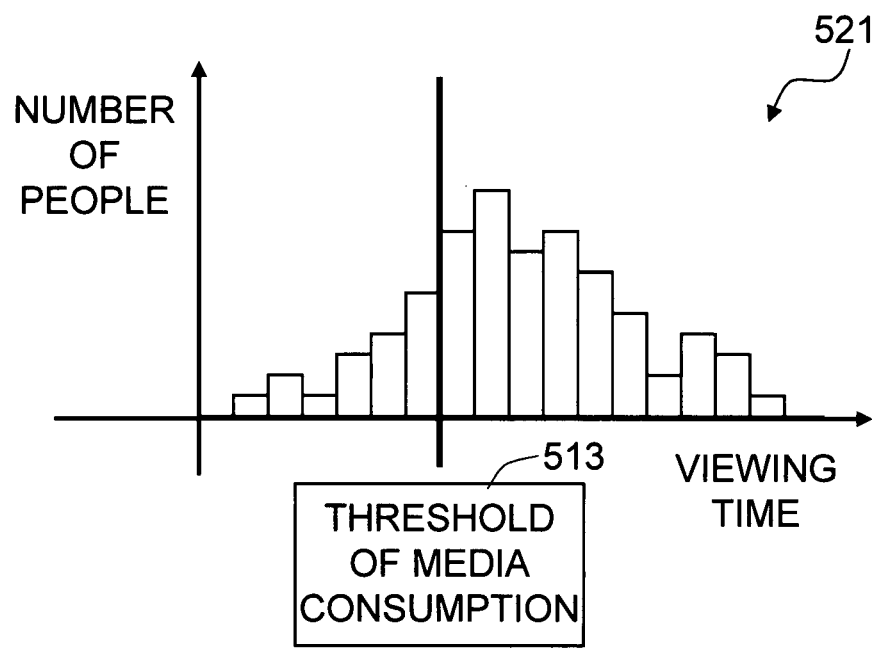
FIG. 10 shows exemplary histograms for counting the number of viewers and average time of viewing, which the embodiment of the present invention can produce as the result of the viewership measurement.
Figure 10:
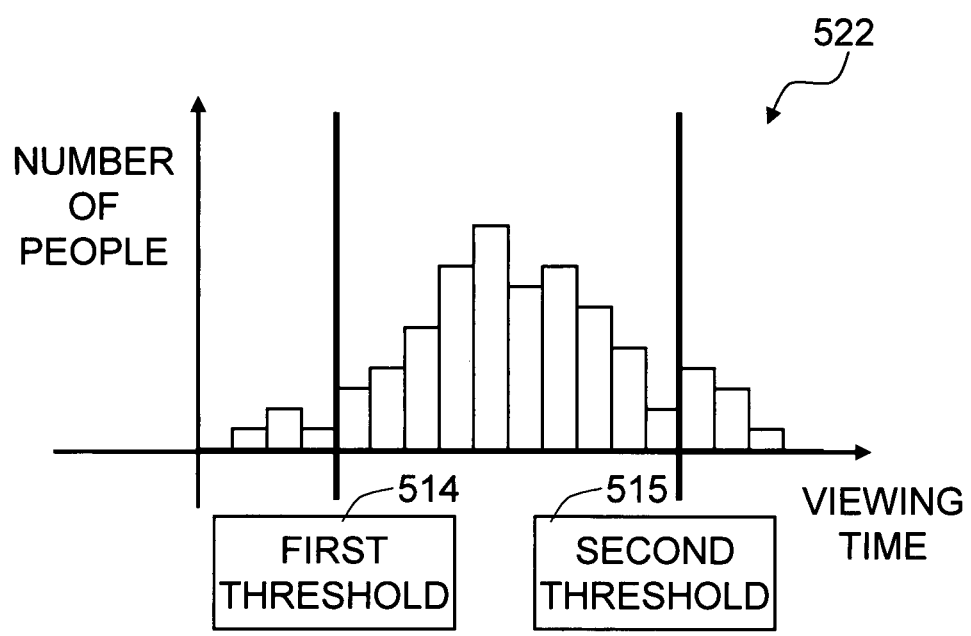

FIG. 10 shows exemplary histograms for counting the number of viewers and average time of viewing, which the embodiment of the present invention can produce as the result of the viewership measurement.

Measurement of the actual viewership for the displayed object 502 (the total number of impressions) is carried out using a forward facing means for capturing images that detects when persons are viewing the screen, such as the first means for capturing images 101 in the exemplary embodiment as shown in FIG. 2.

An impression is counted when a person has looked in the direction of the screen for a predetermined amount of time, as defined in conjunction with client. The threshold of media consumption 513 of "histogram A" 521 shown in FIG. 10 can be an exemplary predetermined amount of time. The sum total of impressions for a displayed object 502 constitutes the actual viewership for that displayed object 502. Measurement of actual viewership provides the basis for establishing the value of a displayed object 502 using traditional media valuation terms such as CPM, or cost per thousand, impressions.

In addition to counting impressions, the present invention provides information about the duration of these impressions. These durations, or impression lengths, are useful in gauging viewer engagement with a particular displayed object 502 or content being delivered at the time of the impression. Network programmers and advertisers can fine-tune their content to match the typical impression length of a given displayed object 502 or series of displayed objects. In the exemplary embodiment shown in FIG. 10, the present invention can further measure the level of attention by using multiple thresholds for the media consumption, first threshold 514 and second threshold 515 in the "histogram B" 522, which are differentiated by the duration of the impressions.

Figure 11:
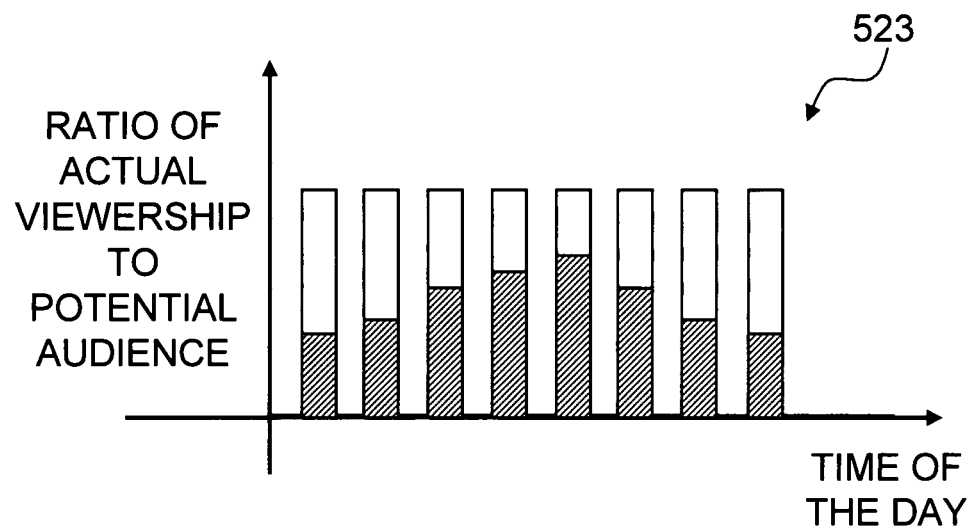
FIG. 11 shows exemplary ratio histograms for the distribution of the viewership during time of day, which the embodiment of the present invention can produce as the result of the viewership measurement.
Figure 11:
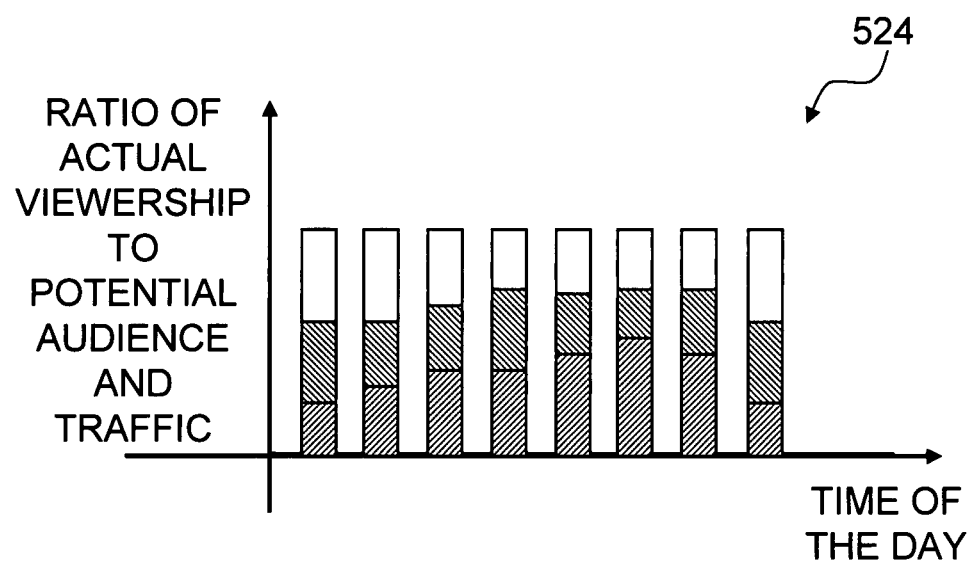

FIG. 11 shows exemplary ratio histograms for the distribution of the viewership during time of day, which the embodiment of the present invention can produce as the result of the viewership measurement. As discussed above for the exemplary embodiment shown in FIG. 2, the present invention measures the potential viewership for a displayed object 502, or those with an opportunity to see, by tracking the behavior of persons around a given displayed object 502. In the past, opportunity to see has been used as a measure of displayed object effectiveness and reach. While the present invention can measure actual viewership, opportunity to see is still a useful measure—particularly when evaluating the ratio of actual viewership to potential audience. In the exemplary embodiment shown in FIG. 11, the "histogram C" 523 shows the ratio of actual viewership to potential audience during time of day. The "histogram D" 524 further shows the ratio of actual viewership to potential audience and to traffic in a space during time of day.

While the above description contains much specificity, these should not be construed as limitations on the scope of the invention, but as exemplifications of the presently preferred embodiments thereof. Many other ramifications and variations are possible within the teachings of the invention. Thus, the scope of the invention should be determined by the appended claims and their legal equivalents, and not by the examples given.

What is claimed is:

1. A method for measuring viewership of viewers for a displayed object, comprising the following steps of:
    capturing a plurality of input images of a plurality of persons in an area where the displayed object is located by means for capturing images;
    applying computer vision technologies and algorithms to the input images using at least a control and processing system;
    detecting faces of the persons in the plurality of input images, wherein persons constitute a plurality of potential, actual and non-viewers;
    placing a set of features of a set of detected faces on standard locations in a set of face image chips for each viewer;
    building a facial appearance model of a viewer by computing the pixel average image of the set of face image chips;
    individually tracking the set of detected faces and keeping identities assigned to the person by generating, maintaining, and terminating tracks of the persons found in the plurality of input images,
    wherein a track of a person is generated when a face of the person is detected,
    wherein the detected face is assigned to the generated track of the person,
    wherein the detected face is compared to an existing face of the generated track, and
    wherein the track is terminated when the detected face disappears from the plurality of input images;
    detecting viewers who looked in the direction of the displayed object for a predetermined amount of time by detecting the number of detected faces with a frontal pose;
    estimating the facial orientation of the detected faces to assess viewership;
    collecting viewership level information data,
    whereby the viewership level information data comprises impressions count of the viewers, average length of impression, distribution of impressions by time of day, and rating of media effectiveness based on audience response;
    segmenting out regions having skin-like color pixel values in the plurality of input images, wherein a machine learning-based face detection approach is employed to detect faces within the regions;
    managing face tracks to find a correct match between a face tracks history and a new input face, using geometric and appearance measurements,
    wherein a geometric match score and an appearance match score are computed for each pair between the new input face and each track from the face tracks history, and
    wherein the geometric match score and the appearance match score measure likelihood of the new input face belonging to each track from the face tracks history; and
    assessing a degree of attention during a viewer's viewing period by computing the proportion of the time when the viewer paid attention to a displayed object out of the total duration of the viewer's face.

2. The method according to claim 1, wherein the method further comprises a step of performing a quantitative and automatic media consumption measurement, based on the measurement of the viewership of the viewers, wherein viewers comprise a plurality of potential, actual and non-viewers.

3. The method according to claim 1, wherein the method further comprises a step of analyzing stopping power of the displayed object based on the viewership of the viewers,
    wherein viewers comprise potential, actual and non-viewers,
    wherein the stopping power is measured by an increased average length of impression, and
    wherein the stopping power of an additional displayed object is measured by an increase in the count of viewers with the additional displayed object.

4. The method according to claim 1, wherein the method further comprises a step of determining a potential viewership for a displayed object wherein the potential viewership is determined by tracking a plurality of behaviors of a plurality of persons around the displayed object.

5. The method according to claim 1, wherein the method further comprises a step of constructing a ratio histogram wherein the ratio histogram compares a potential and actual viewership during time of day.

6. An apparatus for measuring viewership of viewers for a displayed object, comprising:
    at least a means for capturing images that captures a plurality of input images of plurality of persons in an area where the displayed object is located;
    at least a means for video interface; and
    a computer that is programmed to perform the following steps:
    detecting faces of the person in the plurality of input images wherein person constitute a plurality of potential, actual and non-viewers;
    placing a set of features of a set of detected faces on standard locations in a set of face image chips for each viewer;
    building a facial appearance model of a viewer by computing the pixel average image of the set of face image chips;
    individually tracking the set of detected faces and keeping identities assigned to the persons by generating, maintaining, and terminating tracks of the persons found in the plurality of input images,
wherein a track of a person is generated when a face of the person is detected,
wherein the detected face is assigned to the generated track of the person,
wherein the detected face is compared to an existing face of the generated track, and
wherein the track is terminated when the detected face disappears from the plurality of input images;
detecting viewers who looked in the direction of the displayed object for a predetermined amount of time by detecting the number of detected faces with a frontal pose;
estimating the facial orientation of the detected faces to assess viewership,
collecting viewership level information data,
whereby the viewership level information data comprises impression count of the viewers, average length of impression, distribution of impressions by time of day, and rating of media effectiveness based on audience response;
segmenting out regions having skin-like color pixel values in the plurality of input images, wherein a machine learning-based face detection approach is employed to detect faces within the regions;
managing face tracks to find a correct match between a face tracks history and a new input face, using geometric and appearance measurements,
wherein a geometric match score and an appearance match score are computed for each pair between the new input face and each track from the face tracks history, and
wherein the geometric match score and the appearance match score measure likelihood of the new input face belonging to each track from the face tracks history; and
assessing a degree of attention during a viewer's viewing period by computing the proportion of the time when the viewer paid attention to a displayed object out of the total duration of the viewer's face.

7. The apparatus according to claim 6, wherein the apparatus further comprises a computer programmed for extracting viewership level information data, whereby the viewership level information data comprises impression count of the viewers, average length of impression, distribution of impressions by time of day, and rating of media effectiveness based on audience response.

8. The apparatus according to claim 7, wherein the apparatus further comprises a computer programmed for determining a potential viewership for a displayed object wherein the potential viewership is determined by tracking a plurality of behaviors of a plurality of persons around the displayed object.

9. The apparatus according to claim 7, wherein the apparatus further comprises a computer programmed for constructing a ratio histogram wherein the ratio histogram compares potential and actual viewership during time of day.

10. The apparatus according to claim 6, wherein the apparatus further comprises a computer programmed for performing a quantitative and automatic media consumption measurement, based on the measurement of the viewership of the viewer, wherein viewers comprise a plurality of potential, actual and non-viewers.

11. The apparatus according to claim 6, wherein the apparatus further comprises a computer programmed for analyzing stopping power of the displayed object based on the viewership of the viewers,
wherein viewers comprise a plurality of potential, actual and non-viewers,
wherein the stopping power is measured by an increased average length of impression, and
wherein the stopping power of an additional displayed object is measured by an increase in the count of viewers with the additional displayed object.

* * * * *